US006037167A

United States Patent [19]

Adelman et al.

[11] Patent Number: 6,037,167

[45] Date of Patent: Mar. 14, 2000

[54] MAGNETIC POLYNUCLEOTIDE SEPARATION AND ANALYSIS

[75] Inventors: Lonnie W. Adelman; Craig S. Alvis, both of San Diego, Calif.

[73] Assignee: Ericomp, San Diego, Calif.

[21] Appl. No.: 08/908,041

[22] Filed: Aug. 11, 1997

Related U.S. Application Data

[63] Continuation-in-part of application No. 08/316,772, Oct. 3, 1994, Pat. No. 5,656,429.

[51] Int. Cl.[7] .............................. C12M 3/04; C12Q 1/68; G01N 27/76

[52] U.S. Cl. ........................ 435/285.1; 435/6; 435/285.2; 435/286.1; 435/286.2; 435/287.1; 435/287.2; 435/288.6; 435/288.7; 324/201; 324/204

[58] Field of Search ......................... 435/6, 285.1, 285.2, 435/286.1, 286.2, 287.1, 287.2, 288.6, 288.7; 324/201, 204

[56] References Cited

U.S. PATENT DOCUMENTS

| | | | |
|---|---|---|---|
| 3,979,738 | 9/1976 | Feuersanger | 340/174 |
| 4,344,560 | 8/1982 | Iriguchi et al. | 233/19 |
| 4,375,407 | 3/1983 | Kronick | 209/8 |
| 4,736,751 | 4/1988 | Gevins et al. | 128/732 |
| 4,974,660 | 12/1990 | Ernst et al. | 164/465 |
| 5,073,858 | 12/1991 | Mills | 364/413.13 |

OTHER PUBLICATIONS

Wang et al, "Isolation of DNA fragments from agarose gel by centrifugation", Nucleic Acids Res. 22(14);2862–2863, 1994.

*Primary Examiner*—Jeffrey Fredman
*Attorney, Agent, or Firm*—McAulay Nissen Goldberg Kiel & Hand, LLP

[57] ABSTRACT

An apparatus for analyzing a sample of a mixture of compounds selected from the group consisting of polynucleotides, proteins and fragments thereof attached to magnetized moieties which generate a magnetic field contained on a substrate comprising:

a) a support for mounting the substrate, b) a magnetic field detector mounted adjacent the substrate, the magnetic field detector generating an electrical signal in response to a magnetic field from the substrate, c) scanning means for moving the magnetic field detector relative to the substrate, and d) an amplifier operatively connected to the magnetic field detector to amplify a signal generated thereby.

2 Claims, 11 Drawing Sheets

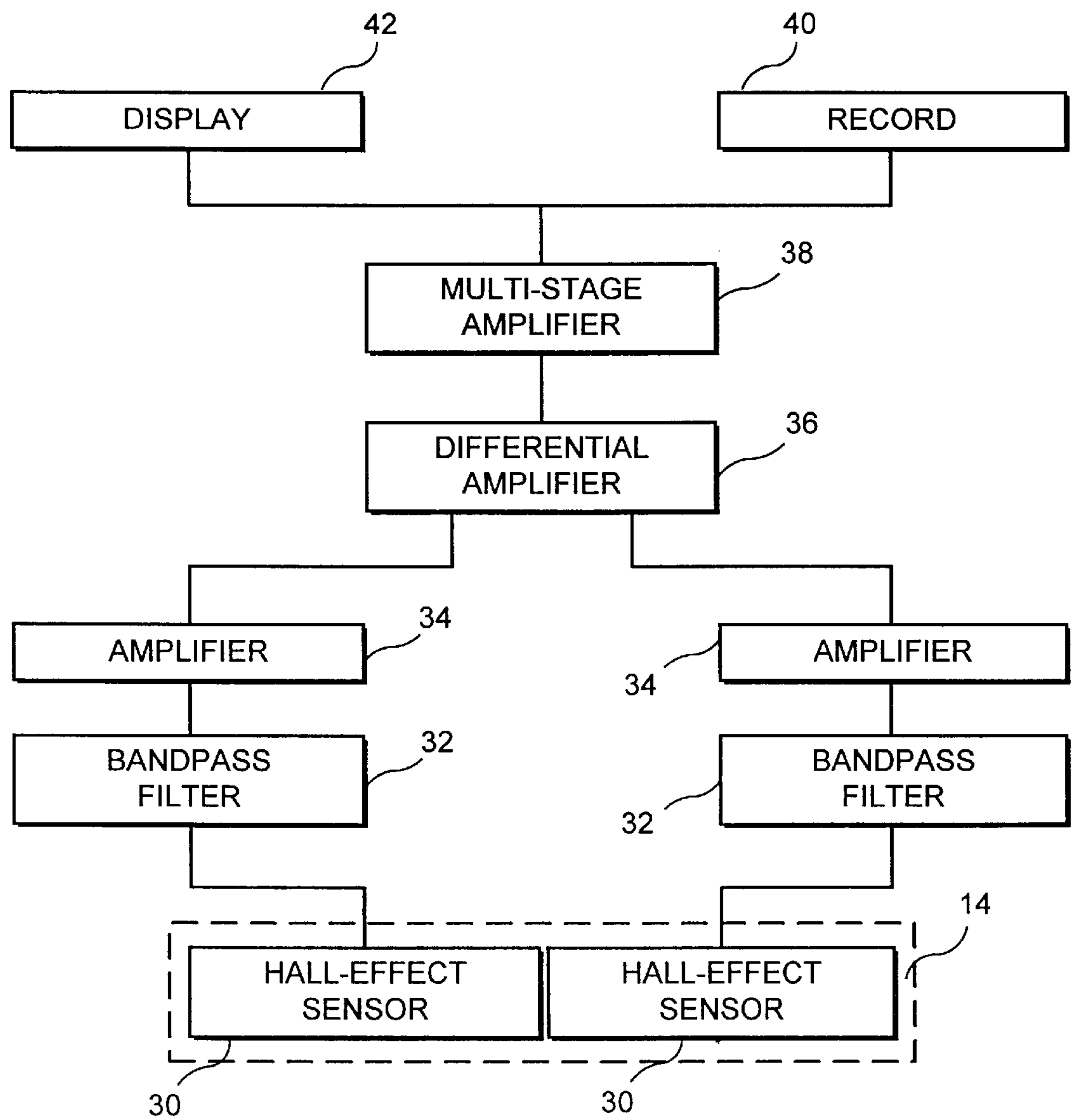
F I G. 2

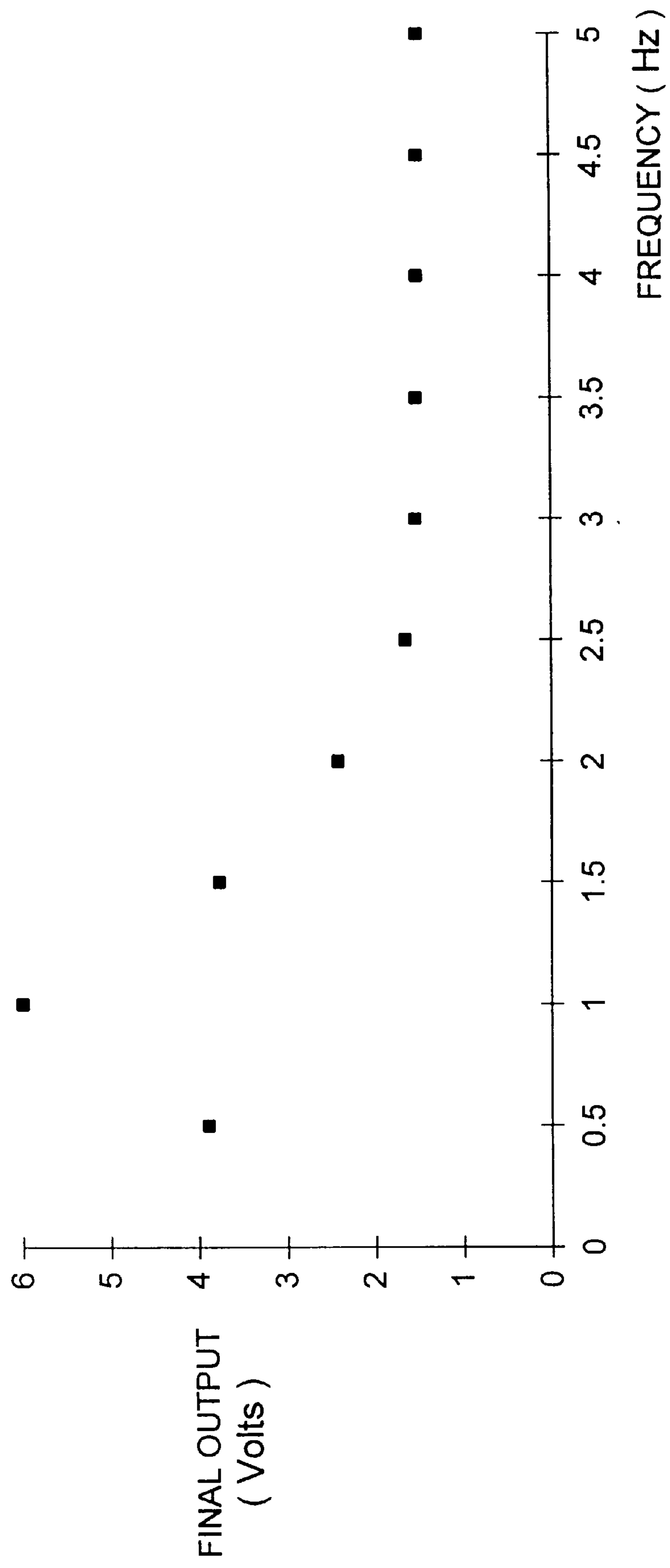
F I G. 5

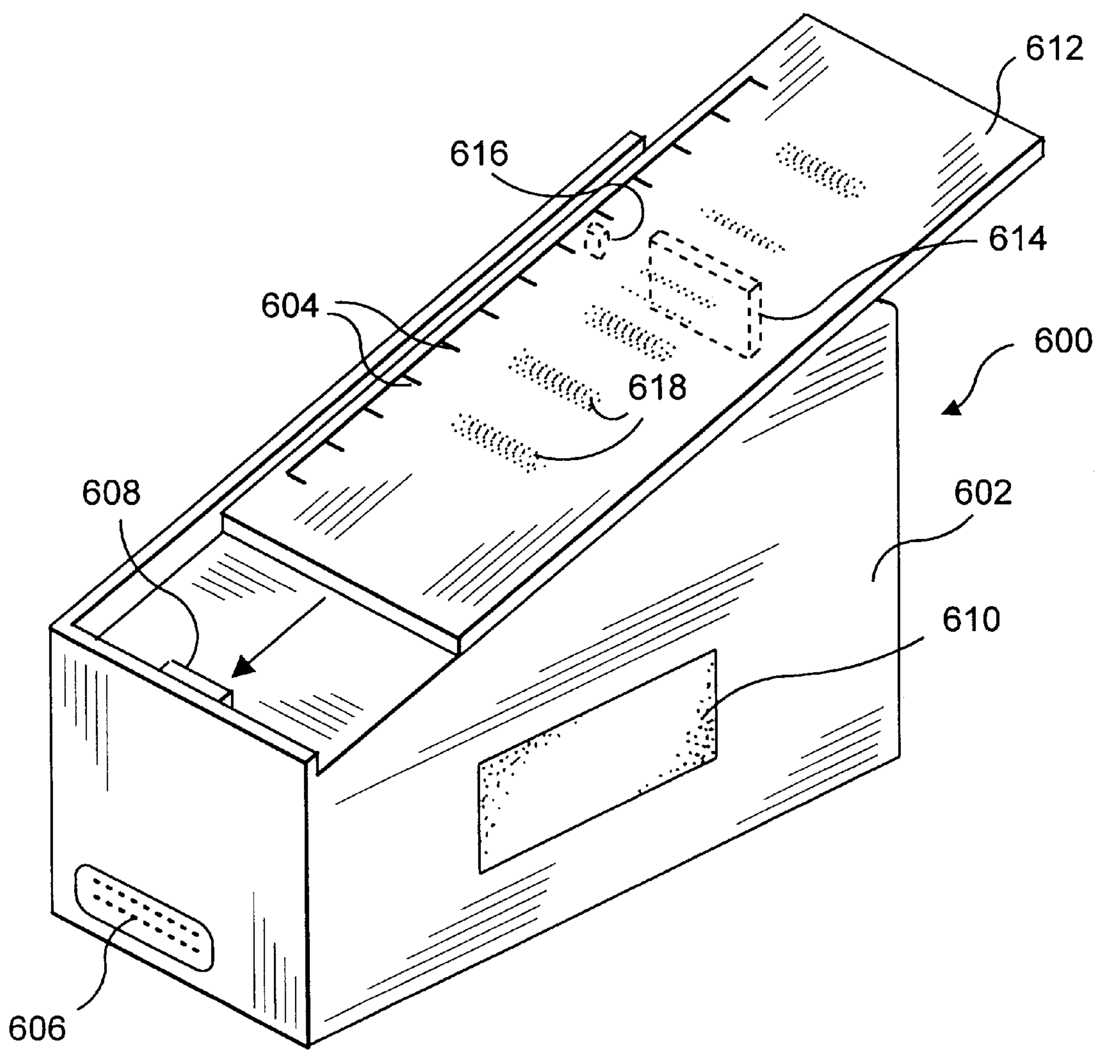
F I G. 6

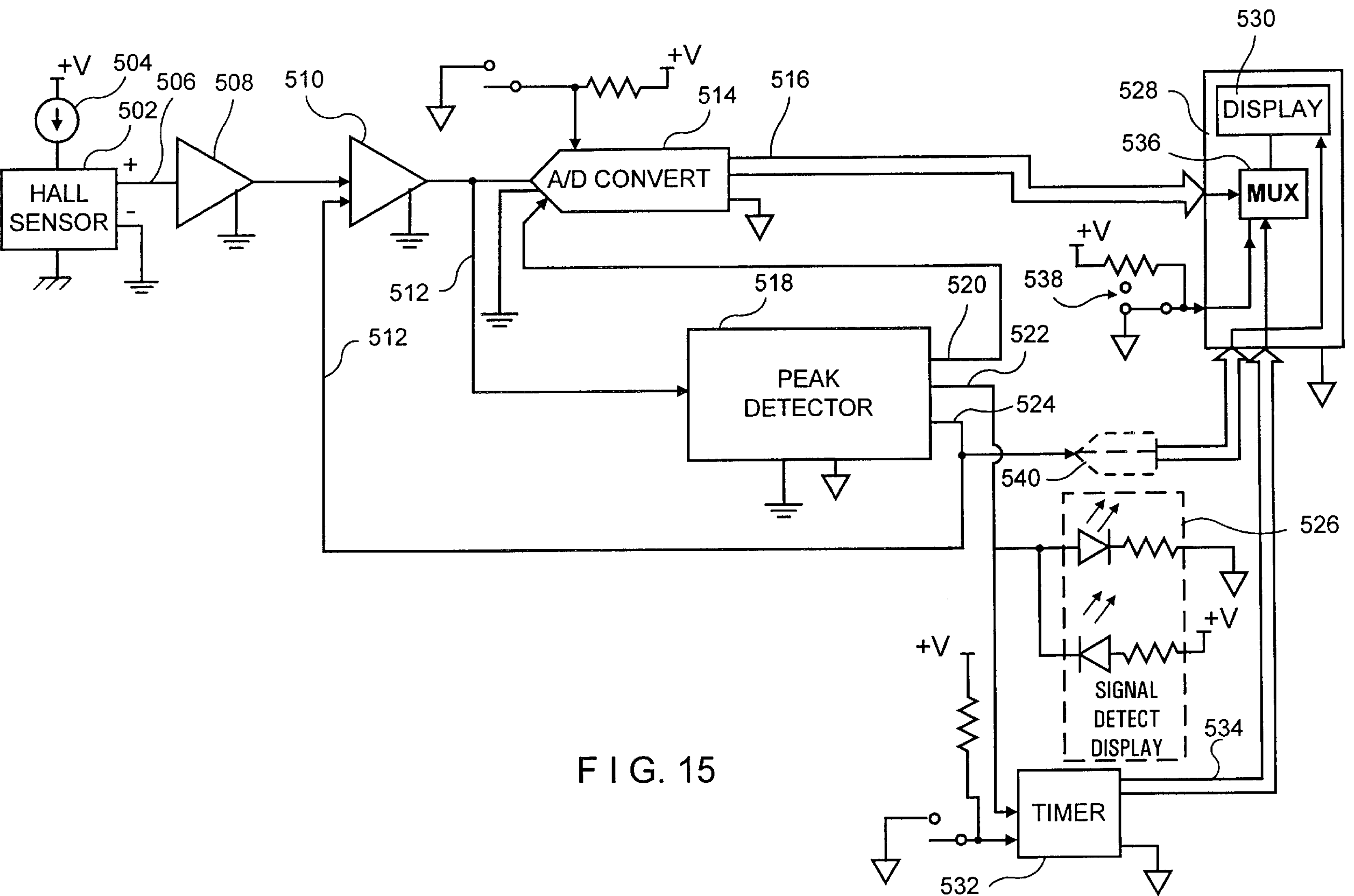
F I G. 15

MAGNETIC POLYNUCLEOTIDE SEPARATION AND ANALYSIS

CROSS-REFERENCE TO RELATED APPLICATION

This is a continuation-in-part of U.S. patent application Ser. No. 08/316,772, filed Oct. 3, 1994, now U.S. Pat. No. 5,156,429 the contents of which are hereby incorporated by reference.

BACKGROUND OF THE INVENTION

The invention relates to the field of sequencing of polynucleotides and/or proteins as well as fragments of such compounds. More particularly, it relates to methods for analyzing their structure and molecular weights.

There is an increasing demand for reliable and inexpensive methods for the sequencing of polynucleotides, such as, DNA, RNA and the like. Generally, a radioactive or fluorescent probe, which selectively hybridizes to a specific target nucleic acid, is added to the support. A typical common type of probe is a single-stranded (ss) DNA which is complementary to a sequence in the target DNA or RNA.

The hybrid molecule thus formed with the label probe thereon may then be detected by various techniques depending on the nature of the label used. An example of such hybridization is shown in U.S. Pat. No. 4,358,535.

Typical labeling probes include the incorporation of a radioactive atom, such as, $^{32}p$, $^{14}C$, or $^{3}H$. This can be achieved by nick translation, such as that shown in Rigbny et al (J. Mol. Biol., 113: 237, 1977), wherein a labeled nucleotide is incorporated into a gap created in the DNA of the probe. Other labels can be introduced by nick translation, for example, by incorporating biotinylated nucleosides which can then be coupled to an avidin bound label, such as, an enzyme. The DNA can also be labeled with antigenic groups reacting with antibodies.

For the assay or quantification of nucleic acids, such as, DNA or mRNA, either the total nucleic acid material present in the sample or that transcribed from a specific gene can be conventionally determined by this so-called dot-blot analysis technique.

One of the problems with such sequencing techniques requires the handling of radioactive isotopes and presents an environmentally undesirable situation in the laboratory. The use of fluorescent labels or enzyme labels results in relatively complicated techniques for the ultimate reading of the label. Generally, expensive equipment and relatively skilled technicians are needed to effect the analysis of gels and/or substrates onto which the labeled molecules or segments have been fixed.

In addition, numerous attempts have been made to automate the electrophoresis step, detection and data handling. However, difficulties have arisen with respect to such methods primarily because of the method of labeling.

The storage and reading of material in magnetic media is widespread with the use of floppy drives, hard drives, and digital and analog tapes. Superconducting quantum interference devices (SQUID) and magnetic force microscopes (MFM) have been in use to measure magnetic fields on microscopic levels. These systems, however, are extremely costly. In addition, both SQUID and MFM devices are limited to the measurement of magnetic fields in materials with extremely smooth surfaces.

SUMMARY OF THE INVENTION

I have discovered a method for sequencing nucleotides which substantially alleviates the problems previously encountered in analyzing mixtures of nucleotides. In particular, I have discovered that by attaching magnetizable moieties to the components of a mixture of such polynucleotides, proteins, and fragments thereof, normally obtained from enzymatic digestion, one can easily determine both the quantity as well as the magnetic size (generally in terms of magnetic weight or dalton size, or base-pairs) of the polynucleotides, proteins and fragments by reading the magnetic field created by the attached magnetizable moieties.

This is accomplished by subjecting the mixture of polynucleotides, proteins and fragments to a separation procedure to distribute the compounds onto a substrate in a pattern or groups, according to their molecular size and quantity. This substrate is then analyzed to determine the molecular size and quantity on the separated groups. Magnetizable moieties are attached to each of the components of the mixture. This attachment may occur prior to subjecting the mixture to the separation procedure or after the separation. The magnetizable moieties are then magnetized by exposing them to a magnetic field. This magnetization step may also take place either before or after the separation procedure is carried out. The thus separated compounds having the attached magnetized or magnetizable moieties thereon are distributed onto a substrate, such that the groups distributed are separated on the substrate according to molecular size and amount. This substrate is then subjected to magnetic reading. Based on the magnetic reading, both the size and amount of each of the groups thus distributed may be ascertained by appropriate calibration methods.

I have further invented a magnetic reader which overcomes the limitations of prior-art magnetic readers, the inventive reader being well adapted in particular for analyzing a distribution of a magnetic compound on a substrate sheet. The apparatus includes a support on which a substrate is mounted. The substrate has a distribution of a magnetizable compound therein. The magnetizable compound being selected from the group consisting of polynucleotides, proteins, and fragments thereof attached to a magnetizable moiety. A magnetic field detector is mounted adjacent the substrate sheet. The magnetic field detector generates an electrical signal in response to a magnetic field originating in the substrate sheet. Scanning componentry is provided for moving the magnetic field detector relative to the substrate sheet. An amplifier is operatively connected to the magnetic field detector to amplify a signal generated by the detector.

The present invention further provides a method for separating a mixture of varying amounts of compounds having different molecular sizes, where the compounds are selected from the group consisting of polynucleotides, proteins, and fragments thereof. Magnetizable moieties are attached to each of the components of the mixture. The mixture is deposited at a starting end of a separation lane. The separation lane provides a resistance to movement of the compounds therealong, the resistance being different for compounds of different molecular sizes. A magnetic field is provided in the separation lane to provide a force on the magnetizable moieties in a direction from the starting end to a terminal end of the separation lane in order to move at least some of the compounds attached to the magnetizable moieties along the separation lane.

In a method according to the present invention for separating a mixture of varying amounts of compounds having different molecular sizes, where the compounds are selected from the group consisting of polynucleotides, proteins, and fragments thereof, magnetizable moieties are attached to each of the components of the mixture. The mixture is deposited at a starting end of a separation lane. The separation lane provides a resistance to movement of the compounds therealong, the resistance being different for compounds of different molecular sizes. A magnet is displaced along the separation lane in a direction from the starting end to a terminal end of the separation lane to entrain at least some of the compounds attached to the magnetizable moieties in movement along the separation lane.

An apparatus is provided for separating a mixture of varying amounts of compounds having different molecular sizes, the compounds being selected from the group consisting of polynucleotides, proteins, and fragments thereof, the compounds having magnetizable moieties attached thereto. A support is provided which has a separation lane therein, the separation lane providing a resistance to movement of the compounds therealong, the resistance being different for compounds of differing molecular size. The separation lane has a starting end and a terminal end. A magnet provides an attractive force on the magnetizable moieties of a mixture deposited in the separation lane. A guide maintains the magnet in proximity to the separation lane, and a drive moves the magnet along the separation lane to entrain at least some of the compounds attached to the magnetizable moieties in movement along the separation lane.

In an apparatus for separating a mixture of varying amounts of compounds having different molecular sizes, a separator wheel is provided which includes a sample reservoir at a central portion thereof for receiving a mixture. The separator wheel further includes a plurality of radial channels in communication with the central reservoir. The radial channels extend outwardly from the central reservoir, each channel having a cross-sectional size different from the cross-sectional size of at least one other channel. A drive is provided for rotating the separator wheel around the central reservoir.

In an apparatus for separating a mixture of varying amounts of compounds having different molecular sizes, a separation medium is provided which is rotatable about a central axis. The separation medium has a sample groove therein for accepting a sample mixture of varying amounts of compounds having different molecular sizes. The sample groove is concentric with the central axis of the separation medium. The separation medium is formed of a gel separation substance. Componentry is provided for rotating the separation medium about the central axis to provide a centrifugal force on the components of the sample mixture, so that the sample components travel outwardly through the separation medium. Sample components of different molecular sizes travel different distances through the separation medium.

In a method for separating a mixture of varying amounts of compounds having different molecular sizes, a separation medium is provided having a central axis and a sample groove concentric with the central axis. The separation medium is formed of a gel separation substance. The sample mixture is deposited in the groove. The mixture includes compounds selected from the group consisting of polynucleotides, proteins, and fragments thereof. The separation medium is rotated about the central axis to generate a centrifugal force on the components of the sample mixture, so that the sample components travel outwardly through the separation medium. Sample components of different molecular sizes travel different distances through the separation medium.

BRIEF DESCRIPTION OF THE DRAWINGS

FIG. 2 is a schematic block diagram of the circuitry of an apparatus for analyzing the distribution of a magnetic compound.

FIG. 5 is a graph showing the frequency response of the amplifier circuit of FIG. 4.

FIG. 6 is a perspective view of an apparatus for analyzing the distribution of a magnetic compound.

FIG. 15 is a schematic circuit diagram of an apparatus for analyzing the distribution of a magnetic compound.

DETAILED DESCRIPTION OF THE INVENTION

Figure 1:
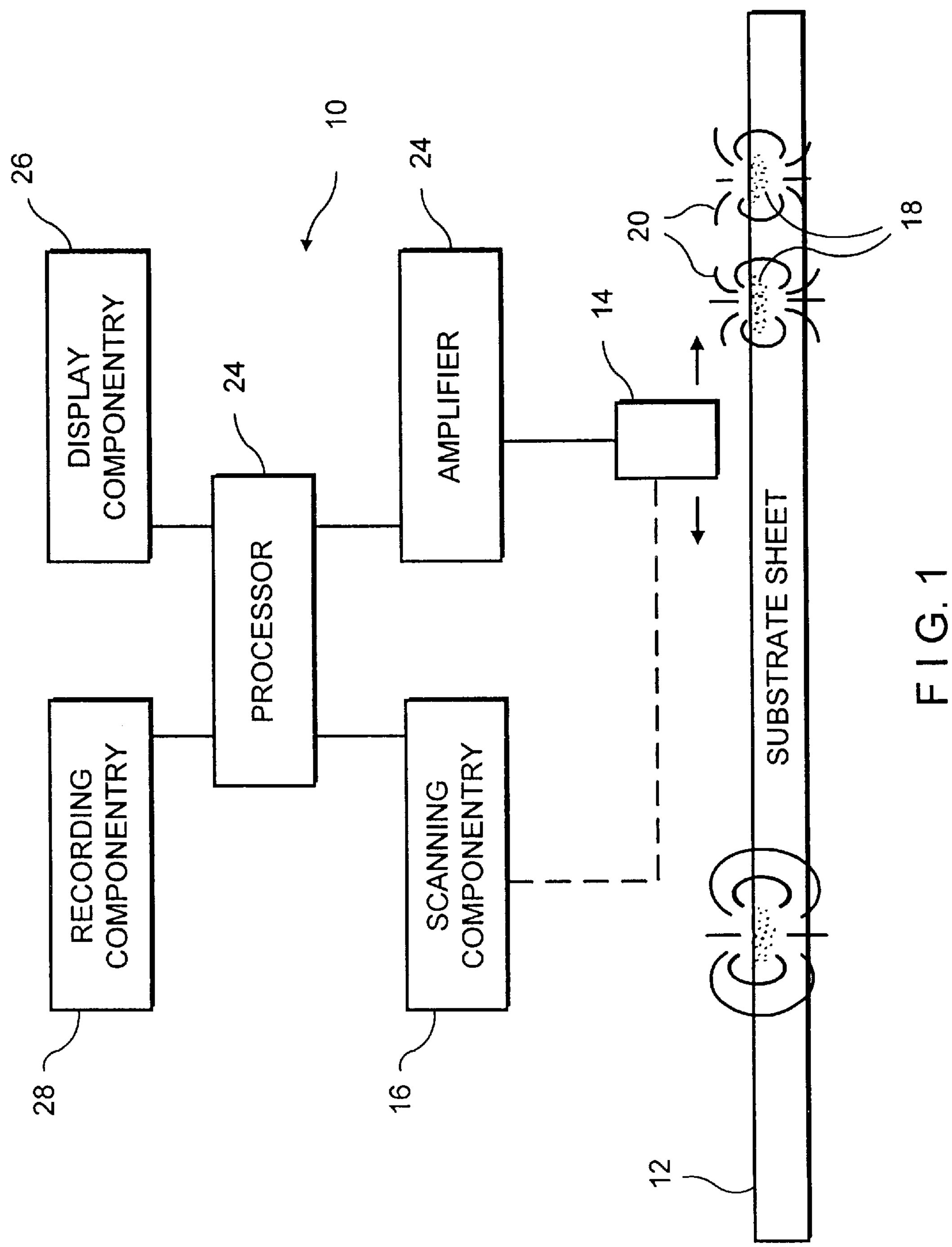
FIG. 1 is a schematic block diagram of an apparatus for analyzing the distribution of a magnetic compound.

The first embodiment of the invention wherein a mixture of varying amounts of nucleotides, proteins and the like, are analyzed will be described in connection with the sequencing of DNA. It is known to subject DNA obtained from cells and the like to digestion with various enzymes which cleave the DNA at different sites. Thereafter, the library obtained from the enzymatically digested DNA is subjected to separation analysis usually by electrophoresis on an agarose or polyacrylamide gel. Such electrophoresis methods are also well known in this art. During electrophoresis, the various segments travel along the gel, usually in a downward direction, depending on the magnetic field applied, and travel relative to their molecular size. Normally, the larger molecular size molecules travel less distance than the smaller molecules. This also can depend on the pore size of the gel and variation of these parameters is well known to the artisan in this field.

At the end of the procedure, the various fragments of the digested DNA are present on the gel in a pattern determined by their distance of travel during the electrophoresis process. The distance of travel is directly related to the molecular size of the fragment. In addition, the size of each group of segments or fragments on the gel is indicative of the amount of the specific component in the original mixture.

I have discovered that the fragments of the digested DNA can be attached to magnetizable moieties, either prior to or subsequent to the electrophoresis process. In the instance where the fragments are attached prior to electrophoresis, the attachment of magnetizable moieties is carried by known procedures, such as, as described in PCT applications WO 92/17609 published Oct. 15, 1992; WO 93/08305 published Apr. 29, 1993; WO 90/06042 published Jun. 14, 1990; and WO 93/20232 published Oct. 14, 1993. See also, PCT/EP90/00454, PCT/GB89/00304, and PCT/EP91/01398. In addition, techniques for attachment of magnetizable moieties are also disclosed in the Technical Handbook Molecular Biology, 1st Ed., Dynabeads Biomagnetic Separation System, published by Dynal International. This brochure describes various methods for the biotinylation of DNA as well as the sequencing of biotinylated DNA. Detailed procedures are presented therein.

The DNA with the magnetic moieties attached thereto as carried out, for example, as described in the above-noted disclosures, is then subjected to magnetization by placement in a magnetic field. The magnetization can be carried out in a conventional manner which is also disclosed in the above Technical Handbook Molecular Biology.

As noted, the magnetization step can be carried out either prior to the electrophoresis analysis by subjecting the mixture of DNA having the magnetic moieties attached thereto to a magnetic field, or after the electrophoresis procedure by subjecting the gel on which the groups of DNA segments having the magnetizable moieties attached thereto have been distributed, by for example, using an electromagnet.

Alternatively, the electrophoresis procedure can by carried out on the digested DNA mixture in the conventional manner. Thereafter, the distributed DNA segments on the gel may be treated so as to attach the magnetizable moieties thereto. In addition, it is possible to carry out the digestion and electrophoresis in the conventional manner and then transfer the groups of electrophoresed DNA segments onto a substrate using conventional Southern blot hybridization techniques. Such techniques are well known in the art and result in the electrophoresed groups of DNA being transferred to a second substrate, usually a sheet.

This sheet, in turn, may be contacted with a sheet containing magnetizable and/or magnetized probes which are selected for specific DNA sequences. The probes thus hybridize to the DNA sequences for which they are selective. This results in a substrate having magnetized or magnetizable portions of groups of DNA segments thereon.

Whichever of the foregoing procedures is used, ultimately a sheet, either of a gel or a transfer sheet as obtained by a blotting method, is produced which contains the distributed DNA segments having magnetized moieties attached thereto. The groups of DNA segments are distributed on the sheet according to their molecular sizes and the sizes of the groups are indicative of the amount of such segments in the original digested mixture.

This substrate may then be subjected to conventional magnetic reading analysis, for example, with devices used to read magnetic cards, magnetic floppy disks, magnetic tapes, and the like. By appropriate calibration techniques, the reading of the magnetic field created by each of the respective groups distributed on the substrate will be indicative of the specific DNA segment as the molecular size of that DNA segment.

In particular, it is clear that such substrates having the magnetized groups thereon, may be formed into the shape of a so-called "floppy disk" and read by computer. Appropriate computer programs can easily be formulated to immediately provide a read-out as to the molecular size and amount of the specific segments being read.

I have specifically discovered that the magnetization of such magnetizable moieties does not disappear after magnetization. That is to say, a residual amount of magnetization remains sufficient to allow reading of the magnetic field of the specific moieties as distributed on the substrate.

By using such magnetic labels for reading, i.e., sequencing DNA and the like molecules, it becomes possible to completely avoid the difficulties which have arisen using the fluorescent, enzyme and radioactive labels of the prior art. In addition, extremely accurate readings of both the molecular size and amount of the segments deposited on the substrate are possible.

In yet another embodiment of the invention, I have found that by using magnetic moieties as primers in a DNA amplification process, one can easily monitor the progress of the amplification process. A variety of methods for DNA amplification which use primers are known in the art. See, for example, the Journal of NIH Research, January 1953, Vol. 5. In an article entitled "PCR's Competitors Are Alive and Well and Moving Rapidly Towards Commercialization", the alternative methods to the so-called polymerase chain reaction are described. These various processes use primer molecules for the purpose of growing entire sequences of DNA. In each of these type processes, it is desirable to have the ability to monitor the progress of the reaction and determine the amount of DNA that has been produced at any given time.

I have discovered a method for facilitating the monitoring of such amplification reactions. Two primers generally act in such amplification procedures to form a single molecule of DNA. The resulting molecule thus produced has a primer at each terminus. When the primers have magnetic moieties attached thereto, each such copy of DNA thus produced will have a magnetizable moiety at each of its terminal points. The magnetic moieties attached to the primers can be subjected to magnetization conditions prior to the amplification reaction to render the moieties magnetic. Alternatively, the mixture during the amplification reaction can be subjected to magnetization conditions, although the former procedure wherein the primers are subjected to magnetization prior to the reaction is preferred.

Normally, the amplification procedures are carried out in receptacles or containers, such as small test tubes and the like. The test tubes containing the reaction mixtures are placed in an appropriate temperature cycling device which subjects these mixtures to the multiple temperature cycles required for the amplification procedure.

At an interim time during the amplification procedure, the contents of the receptacle, i.e., the reaction mixture can be subjected to a magnetic field, i.e., by use of an electromagnet to separate the magnetized primer elements from the formed DNA sequences having the magnetizable moieties at each terminus. Normally, in a tube which is held in a vertical position, if the electromagnetic field is positioned close to the bottom of the tube, the primers, being lighter than the completed strands of DNA, travel faster than the completed strands within the reaction mixture and collect at the bottom of the tube. This leaves the completed DNA strands with the magnetized moieties at the respective terminus ends in a position toward the tube midpoint.

Using appropriate known devices, the size of the magnetic field created by the produced sequences, can be measured. This can be easily correlated to the total amount of DNA which has been produced at that point. Typical of devices which can be used to measure the magnetic field created by the completed DNA sequences are so-called "Hall" sensors. See *Sensors*, March 1986, published by North American Technology. Such so-called Hall sensors, when placed in a magnetic field oriented at right angles to the Hall current, measure a voltage output which is in direct proportion to the strength of the magnetic field. The measurement of the magnetic field thus produced by the completed DNA copies can easily be correlated by appropriate predetermined correlation charts to the amount of DNA produced from the amplification procedure. Of course, other types of devices which can measure Hall effect sensors can be used.

EXAMPLE

Commercially available biotinylated DNA fragments were incubated with Streptavidin coated magnetizable particles at room temperature for one hour with occasional shaking. Separate runs with 10 nm and 50 nm particles were conducted. The bound samples as well as unbound DNA controls were loaded onto gels, either acrylamide or agarose, and electrophoresed for a time sufficient to allow separation of DNA fragments.

After completion of the run, the electrophoresis assembly was dismantled and the gel removed. One set of duplicate samples of bound and unbound DNA was stained with ethidium bromide and visualized under UV light. The other portion of the gel containing twin bound and unbound DNA was analyzed using a magnetic detection system.

The procedure for magnetic detection was carried out by placing the wet or dry gel on a manually controlled one-axis positioning system. The positioning system with the attached gel was then placed under a sensor assembly consisting of a Hall-effect sensor. The output of the sensor was DC amplified and the AC coupled to several stages of amplification. The total gain of the amplification was approximately 10,000. The output of the final amplification detection connected to an oscilloscope for visual detection. When a group of bound DNA was positioned under the sensor, a large voltage swing may be seen on the oscilloscope.

Both DNA bound to 50 nm avidin-coated particles as well as DNA bound to 10 nm particles provided detectable bands corresponding to the bands detected in the ethidium bromide-stained lane.

In carrying out the above experiment, a series of samples of avidin coated beads with or without attached biotinylated DNA was prepared. The DNA utilized was a commercial library obtained from Life Technologies Inc. of Frederick, Md., Catalogue No. 15616-014, Lot No. HEW709. This sample consists of a HIN F I-Digested ϕx 174RF DNA with biotin-14-dATP.

Run A

A series of samples was prepared as follows:

Sample A1: 5λ of 50 nM Avidin coated beads (MB)

Sample A2: 5λ MB +5λ of DNA (ϕX)

Sample A3: 5λ ϕX

Sample A4: 5λ of 10 nM Avidin coated beads (EB)

Sample A5: 5λ EB+5λ ϕX

All samples were incubated at room temperature for one hour with occasional shaking. The gel was prerun at 450V, 6mAmps, and 19.2 watts for one hour.

To Sample Nos. A1, A3 and A5, 5λ of water was added. 10λ of a loading buffer (LB) consisting of 80% deionized formamide, 10 mM EDTA, 1 mg/ml xylene cyanol FF and 1 mg/ml bromophenol blue were added. The gel running buffer was composed of 89 mM of tris/89 mM boric acid/2 mM EDTA. Two separate electrophoresis gel runs were made with a load of 10λ per lane. Duplicate series were run on each half of the gel. Thus lanes 2 through 6 were loaded with Sample Nos. A1, A2, A3, A4 and A5 respectively, and similarly, lanes 9, 11, 13, 15 and 17 were loaded with Sample Nos. A1 through A5, respectively. The electrophoresis run was conducted at 450V, 26.8 mAmps, and 12.6 watts for 55 minutes.

At the conclusion of the run, that side of the gel having lanes 2 through 6 was stained with ethidium bromide. That side of the gel containing lanes 9 through 17 was dried by placing the gel onto drying paper and drying the gel-paper combination in a drying apparatus. The dried gel-paper combination was covered with a plastic film (SaranWrap).

Run B

A second series of samples was electrophoresed for a longer period of time. The sequencing gel was prepared in the same manner and the following Samples were prepared:

Sample B1: 5λ EB

Sample B2: 5λ ϕX

Sample B3: 5λ ϕX+5λ EB

All Samples were incubated at room temperature for one hour with occasional shaking. The gel was prerun at 450V, 39.4 mAmps, and 18.7 watts for 45 minutes.

To Samples B1 and B2, 5λ of water was added. 10λ of loading buffer (LB) was added to each Sample and the Samples were heated and 90° C. for three minutes and cooled on ice for two minutes. 10λ of samples was loaded per lane. The gel was again divided into two sides. Sample B1 was loaded at lanes 3 and 13, Sample B2 was loaded at lanes 6 and 16, and Sample B3 was loaded at lanes 9 and 19. The run was carried out for one hour and 15 minutes. The side containing lanes 3, 6 and 9 was dried and the side containing lanes 13, 16 and 19 was stained with ethidium bromide.

Photographic Analysis of Runs A and B

Photographs under ultraviolet light were taken of the ethidium bromide stained gel portions from Run A and Run B. In a photograph of the Run A gel, it is clear that the DNA attached to ferric oxide of Sample A2 has progressed through the gel. The lane of Sample A2 showed a clear correspondence with the lane of Sample A3, which was unbound DNA. Sample A5, also unbound DNA, showed bands corresponding to those of Sample A3.

A photograph under ultraviolet light of Run B showed better spreading with a longer electrophoresis time. It was clear that Sample B3 of DNA attached to ferric oxide moved through the gel in a manner similar to the DNA alone of Sample B2.

Table 1 shows the measurements of the separation of the bands for Sample B2, i.e., unbound biotinylated DNA. Please note that for the Tables, all measurements are reference to the position of the gel image corresponding to the bottom of the well of the undried gel.

TABLE 1

| Band Number | Band Size (Bases) | Distance from Reference Position to Band (mM) |
|---|---|---|
| 1 | 726, 713 | 17 |
| 2 | 533 | 21 |
| 3 | 500 | 23 |
| 4 | 427, 417, 413 | 28 |
| 5 | 311 | 34 |
| 6 | 249 | 39 |

TABLE 1-continued

| Band Number | Band Size (Bases) | Distance from Reference Position to Band (mM) |
|---|---|---|
| 7 | 200 | 40 |
| 8 | 151 | 48 |

Table 2 shows the measurements for Sample B3 of DNA attached to ferric oxide:

TABLE 2

| Dot Number | Assumed Corresponding Band Size (Bases) | Distance from Reference Position to Band (mm) |
|---|---|---|
| 1 | | 6 |
| 2 | | 8 |
| 3 | 726, 713 | 17 |
| 4 | 533 | 21 |
| 5 | 427, 417, 413 | 26 |
| 6 | 427, 417, 413 | 29 |
| 8 | 311 | 31 |
| 9 | 311 | 34 |
| 10 | 200, 249 | 36 |
| 11 | 151 | 48 |

In Table 2, it is believed that Dot Nos. 1 and 2 represent noise. However, it is clear that Dot No. 3 has picked up the bands of 726 and 713 bases (Table 1) at a distance of 17 mm from the well. It is believed that the remainder shows the spreading of the bands corresponding to the bands of unbound DNA in lane 13. This shows that the bound DNA moves through the gel in a manner corresponding to the movement of the unbound DNA.

Magnetic Analysis of Runs A and B

The dried gel-paper-plastic film combination from Example 1 was positioned under the magnetic detector device. At each instance where a voltage swing was observed on the oscilloscope, a mark was made. This was done for each of lanes 9, 11, 13, 15 and 17, respectively.

The magnetic detection process on the gel of Run A showed that there was travel of the particles through the gel. In addition, DNA bound to the 10 nM particles also travel through this gel and can be detected by the magnetic sensor. The band structure observed with the magnetic detector was seen to correlate to the bands of bound DNA detected photographically. These results were confirmed with magnetic detection of the band structure of the gel of Run B.

As illustrated schematically in FIG. 1, an apparatus 10 is provided for analyzing the distribution of a magnetizable compound on a substrate sheet 12. The magnetizable compound has been separated (by electrophoresis, for example) into a number of different bands 18. The substrate sheet 12 may be a gel such as agarose or acrylamide, preferably dried, or any porous material or other blotting material capable of holding separated bands a magnetizable compound.

Each band 18 of magnetizable compound is subjected to a magnetic field to magnetize the compounds, giving each band a magnetic field 20, and resulting in a magnetic field distribution across the surface of the substrate sheet 12 which is proportional to the distribution of the magnetized compounds in the substrate sheet 12. A magnetic detector 14 is mounted in proximity to the substrate sheet 12 and is connected to scanning componentry 16 to move the magnetic detector 14 across substrate sheet 12 and through the magnetic fields 20 generated by the bands 18 of magnetizable material. Alternately, the substrate can be moved and the detector held static. The output of magnetic detector 14 is passed to amplifier circuitry 22, which generates a signal representative of the field detected by magnetic detector 14 and passes that signal on to a processor 24. The processor 24 reads the magnetic field signal as well as a signal from the scanning componentry representing the position of the magnetic detector 14 to generate a map of the magnetic field across the substrate sheet 12. The processor 24 may be a component of a general-purpose electronic computer programmed to process signals from the amplifier 22 and the scanning componentry 16.

The magnetic field map may be stored by recording componentry 28, for example, in a computer memory or by a hard copy printout. The map may further be displayed on a display 26, such as a computer monitor.

As illustrated in FIG. 2, the magnetic field detector 30 is in one embodiment composed of a pair of Hall-effect sensors. One of the sensors is mounted in proximity to the substrate sheet 12, within the magnetic field of the bands 18, while the other is mounted at a distance from the substrate sheet 12, generally of a few centimeters, to be outside of the magnetic field of the bands 18. A signal from each Hall-effect sensor is separately filtered 32 and amplified 34, after which both signals are fed to a differential amplifier 36, which generates a difference signal representing the difference between the magnetic fields sensed by the two Hall-effect sensors. The difference signal is then amplified by a multi-stage amplifier 38 for recording 40 and/or display 42 of the amplified difference signal. The use of a pair of magnetic field sensors 30 to generate a difference signal results in the rejection of common-mode magnetic interference (noise), such as interference from electrical power supplies.

Figure 2A:
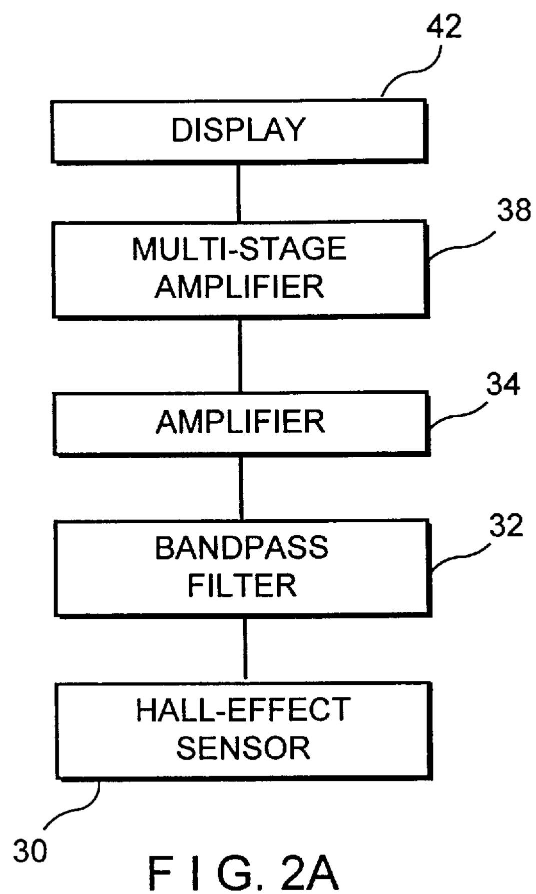
FIG. 2A is another embodiment of a schematic block diagram of the circuitry of an apparatus for analyzing the distribution of a magnetic compound.

Another embodiment is a device similar to that of FIG. 2 but wherein the amplifier, bandpass filter, and amplifier on the right and, if desired, the differential amplifier are not used. Accordingly, the amplifier on the left feeds directly into the multi-stage amplifier. This embodiment is shown in FIG. 2A. While the bandpass filters 32 are illustrated schematically as a separate stage from the amplifier stages 34, 36, and 38, it is to be understood that the filtering of frequencies in general takes place throughout the amplification process, resulting in an amplifier frequency response profile. The frequency response of the combination of filters 32 and amplifier stages 34, 36, and 38 preferably has a peak at around 1 Hz with a bandwidth of approximately 1.5 Hz. The peak frequency and bandwidth may be tailored to particular magnetic reading applications. In general, however, it is preferable for the filter/amplifier circuitry to be unresponsive to frequencies at or above 60 Hz to avoid the substantial level of magnetic interference caused by standard A/C power lines. Furthermore, in order to avoid interference related to audio frequencies (i.e. around 20 Hz to around 20 kHz), the filter/amplifier circuitry is preferably unresponsive to frequencies above around 20 Hz). It is important that overall, the filter is set up to reject interference from outside electrical and magnetic sources.

Figure 3:
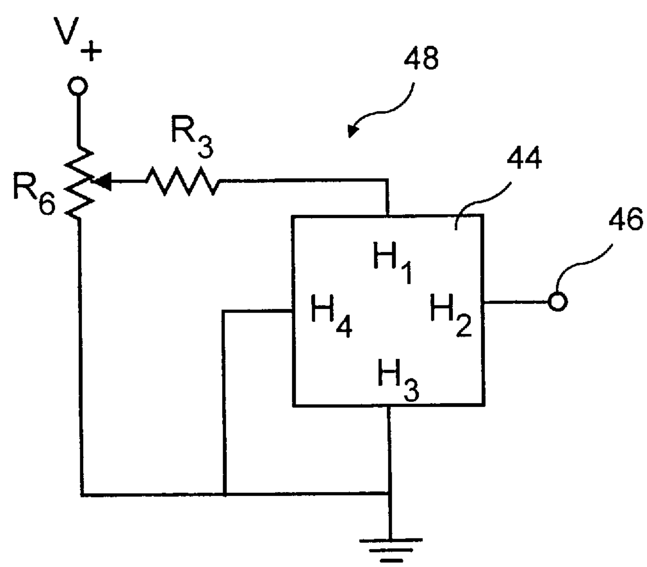
FIG. 3 is a circuit diagram of a Hall-effect sensor for use with an apparatus for analyzing the distribution of a magnetic compound.

One Hall-effect sensor useful as sensor 30 is the InSb Hall Generator No. 327869 of F. W. Bell, Orlando, Fla. A sensor circuit 48 employing a Hall-effect sensor 44 is illustrated in FIG. 3. A constant electrical current is supplied by resistors R3 and R6 between terminals H1 and H3 of the Hall-effect sensor 44. A magnetic field passing through the Hall-effect sensor generates a voltage between terminals H2 and H4. A signal output 46 is wired to terminal H2.

Figure 4:
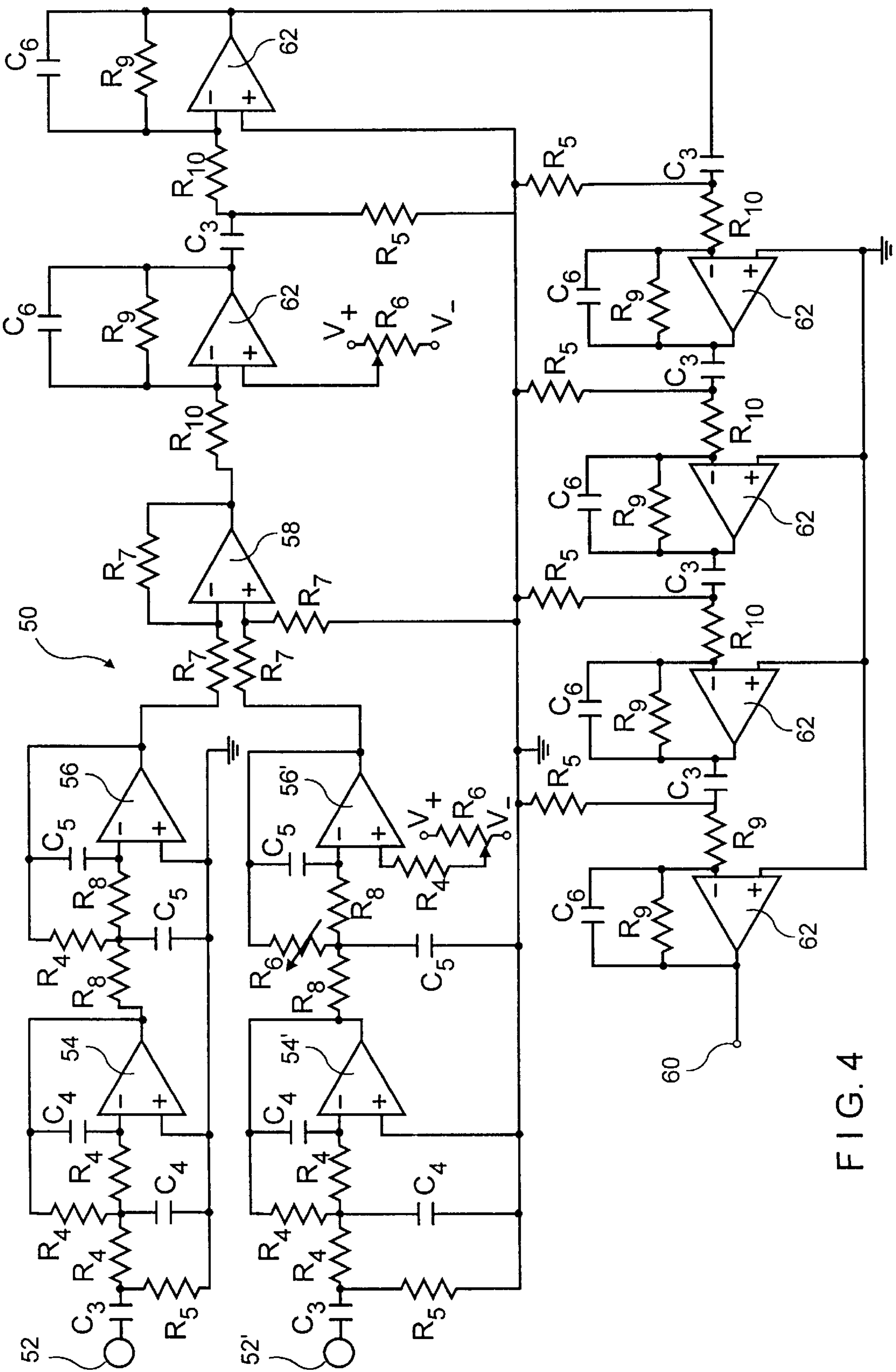
FIG. 4 is a circuit diagram of an amplifier circuit for use with an apparatus for analyzing the distribution of a magnetic compound.

In FIG. 4, a circuit 50 is provided to amplify and filter a signal from a pair of Hall-effect sensors. the output 46 of one sensor circuit 48 is connected to a first signal input 52, and the output 46 of another sensor circuit 48 is connected to a second signal input 52'. Inputs 52, 52' are capacitively coupled to respective first-stage op-amps 54, 54', the outputs of which are coupled to respective second stage op-amps 56, 56'. The outputs of second-stage op-amps 56, 56' are coupled to differential amplifier 58, the output of which is in turn amplified by multiple amplifier stages 62 to generate an amplified differential signal output at a terminal 60. Capacitors and resistors in circuit 50 provide feedback in the op-amp circuits, coupling between stages of the amplification, and passive filtering of the signal. Useful values of capacitors and resistors in circuits 48 and 50 are as follows:

| Component | Value |
|---|---|
| R1 | 15 K |
| R2 | 56 K |
| R3 | 470Ω |
| R4 | 15 K |
| R5 | 34 K |
| R6 | 10 K variable, 10 turns |
| R7 | 10 K |
| R8 | 10 K |
| R9 | 102 K |
| R10 | 3.01 K |
| C1 | 100 μF |
| C2 | 4700 μF |
| C3 | 33 μF |
| C4 | .01 μF |
| C5 | .33 μF |
| C6 | 2.35 μF |

The frequency response of amplifier circuit 50 is illustrated in FIG. 5. Amplifier circuit 50 is primarily responsive to frequencies between 0.5 and 1.5 Hz, with a peak response at approximately 1 Hz.

In response to a magnetic field alternating at 1.0 Hz detected by sensor 48, amplifier 50 exhibits a substantially linear output of approximately 2 Volts per Gauss of magnetic field.

The frequency response of a magnetic detector including sensor 48 and amplifier 50 can be tailored to different applications. A peak frequency response of 1.0 Hz is ideal where the rate at which the detector 14 is scanned across the substrate (in mm/sec, for example) divided by the average width of the magnetized bands 18 (in mm, for example) is on the order of 1.0 $sec^{-1}$. In general, the ideal frequency response peak $f_{peak}$ is related to scanning rate v and band width $w_{avg}$ by the equation $f_{peak} \approx v \div W_{avg}$.

An advantage of the A-C-coupled amplifier circuit of FIG. 4 is that it is substantially unresponsive to magnetic fields which are constant or vary at low frequencies, e.g., the earth's magnetic field, and error voltages from the sensor which are low frequency in nature.

An analyzing apparatus 10 (FIG. 1) may include magnetic field sensors other than Hall-effect sensors, such as magneto-resistive sensors or inductive magnetic field sensors. As noted, the circuit can include a second sensor to eliminate interference.

FIG. 15 illustrates another circuit diagram for the analyzing apparatus 10 of FIG. 1. In this circuit 510, a single Hall-effect sensor 502 is used to detect the magnetic field of the bands 18. The Hall-effect sensor 502 is supplied with a constant current from a current source 504 and generates a voltage output at a terminal 506 proportional to the magnetic field detected by the sensor 502. A buffer 508 receives the output of the sensor 50. Buffer 508 is preferably a single-stage amplifier with a fixed gain of unity, a passband of 1 kHz, a two-pole filter response, and bipolar output swing. The output of the buffer 508 is fed to an amplifier 510. The gain of the amplifier 510 is around 107, but the gain is variable by decades in response to input from the gain control line 512. The amplifier 510 has a 6–8 pole filter which passes frequencies between approximately 0.5 and 1.5 Hz, but this may vary depending on other factors.

The amplified signal from the amplifier 510 is fed to an analog-to-digital converter 514, which converts the amplified analog signal to a digital signal output on signal lines 516. The amplified signal from the amplifier 510 is also fed to peak detector circuitry 518. The peak detector circuitry 518 has a peak detect output 520, a signal detect output 522, and a gain control 524.

The gain control 524 operates the gain control line 512 to control the gain of the amplifier 510, such that when the peak detector 518 detects an excessively high signal level from the output of the amplifier 510, the gain control 524 lowers the gain of the amplifier 510, by one decade, for example. Similarly, when a low signal level is detected by the peak detector 518, the gain control 524 increases the gain of the amplifier 512.

The signal detect digital output 522 is high as long as the peak detector 518 detects a signal (above a predetermined threshold), and low when no signal is detected. A signal detect display 526 includes a green LED **526*a* which is illuminated when the signal detect output is high (indicating signal detection) and a red LED 526*b*** which is illuminated when the signal detect output is low (indicating no signal detection).

The signal detect output 522 is further fed to a timer 532. When the signal detect output 522 goes high, the timer 532 begins counting, and when the signal detect output 522 goes low, the timer stops counting. The timer 532 thus measures the duration of a magnetic field signal detected by the Hall-effect sensor 502 and asserts the result on lines 534. The duration of the signal is proportional to the width of a detected band 18 of magnetizable compound, the width being the signal duration as measured by the timer 532 multiplied by the speed at which the Hall-effect sensor 502 is scanned across a substrate sheet.

The peak detect output 520 of the peak detector 518 is activated when a peak is detected in the amplified signal output of the amplifier 510. The A/D converter 514 is responsive to a signal from the peak detect output 520 to hold the signal corresponding to the peak value on the output lines 516.

A display system 528 is provided, which includes a display device 530, such as an LCD or LED digital display along with an appropriate display driver. The display system 528 selectively displays either the value of the signal peak, as asserted on lines 516, or the duration of the signal, as asserted on lines 534. Both of those signals are fed to a demultiplexer 536. A display select switch 538 selects which of the signals is fed by the demultiplexer 536 to the display device 530. The gain control output 522 of the peak detector 518 is also fed to the display device 530 to place the displayed decimal point in the proper position corresponding to the gain of amplifier 510 (i.e., for each decade increase in amplifier gain, the decimal point is moved one position to the left). Where the gain control 524 has an analog output, an analog-to-digital converter 540 is used to provide the display device 530 with a digital signal.

In one embodiment of the analyzing apparatus 10, the substrate sheet 12 is mounted in a stationary position and magnetic field detector 14 is scanned across the surface of the sheet 12. In an alternative embodiment, magnetic field detector 14 is stationary while the substrate sheet 12 is moved by the scanning componentry 16. The field detector 14 may be moved across substrate 12 along a plurality of parallel paths to generate a two-dimensional scan of the substrate.

In another embodiment 600 (FIG. 6) of the analyzing apparatus 10, the scanning motion is performed manually, with scanning componentry 616 being provided to detect the position of the substrate sheet 612 relative to the magnetic detector 614. The substrate 612, in which bands of magnetizable material 618 are present, is slid across a detector base 602. The magnetic detector 614 is mounted in the base 602. These timing markings can also indicate position, velocity, and acceleration for the purposes of syncing-up with the sample. The substrate sheet 612 is provided with a plurality of timing markings 604 which are detected by the scanning componentry 616, such as an optical detector, to detect movement of the substrate sheet across the detector base 602. An end sensor 608 detects contact with the substrate 612 to indicate the end of a scan. A display 610, such as an LED or LCD display, is provided to display information regarding the scan, and a data port 606 is provided to exchange data between analyzing apparatus 600 and a computer system. The data port may be optical, magnetic/inductive or any other type of data transmission port known for such purposes to the skilled artisan.

Figure 7:
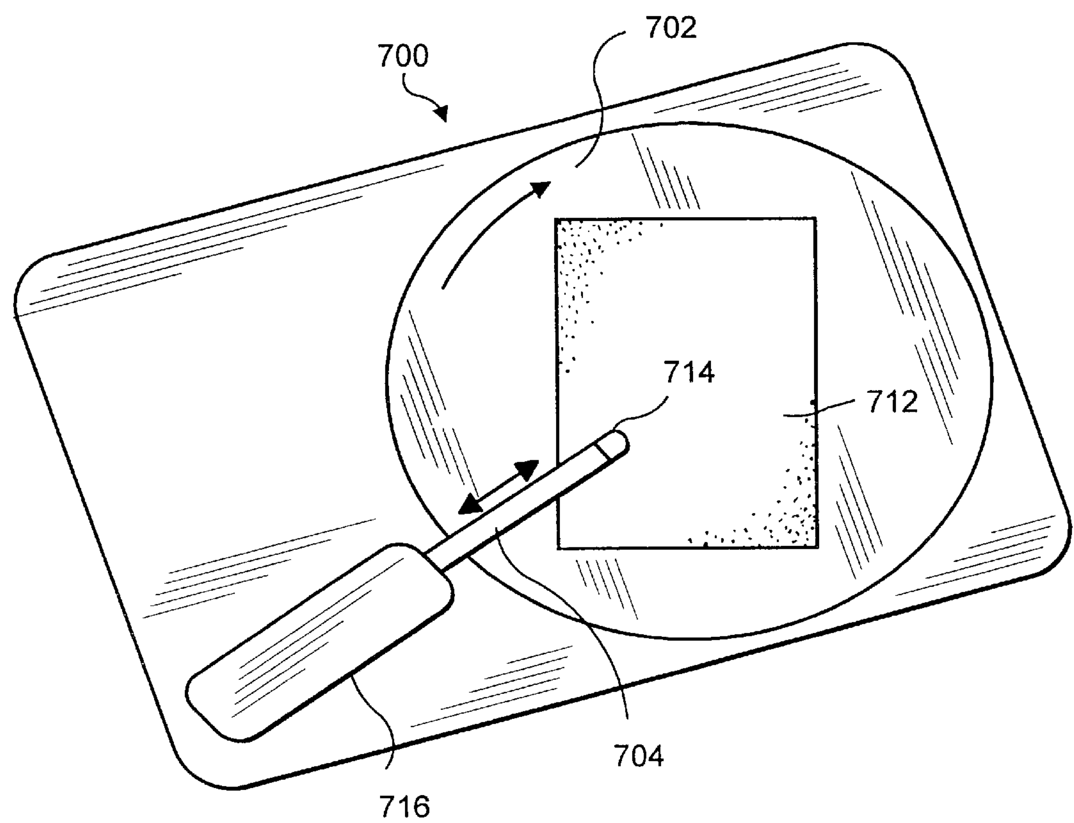
FIG. 7 is a plan view of another apparatus for analyzing the distribution of a magnetic compound.

In another embodiment 700 (FIG. 7) of the analyzing apparatus 10, a substrate 712 is mounted on a rotating platform 702. A magnetic field detector 714 is mounted on a detector arm 704. The radial position of detector arm 704 is controlled by a linear scanning motor 716. In a scan of substrate 712, the platform 702 is rotated, thus rotating the substrate 712, and the detector arm 704 is moved to select the radial position of magnetic detector 714. By rotating the substrate 712 at a high rate, similar to the rotation of magnetic disk drives, the analyzing apparatus 700 can quickly and accurately read the magnetic field of the substrate 712.

Various other embodiments of the analyzing apparatus 10 are possible. For example, the substrate may be a liquid, with suspended magnetizable compounds being separated by gravity, centrifuge, or otherwise, in a test tube or capillary tube. The magnetic field detector 14 can the be scanned across the tube to record the magnetic field. In light of this disclosure, various additional embodiments will be apparent to those of ordinary skill in the art.

Magnetic Separation

The inventor has discovered that mixtures of compounds of varying molecular weight, such as polynucleotides, proteins, and fragments thereof, can be separated by attaching magnetizable moieties thereto and applying a magnetic field to the compound.

Figure 8:
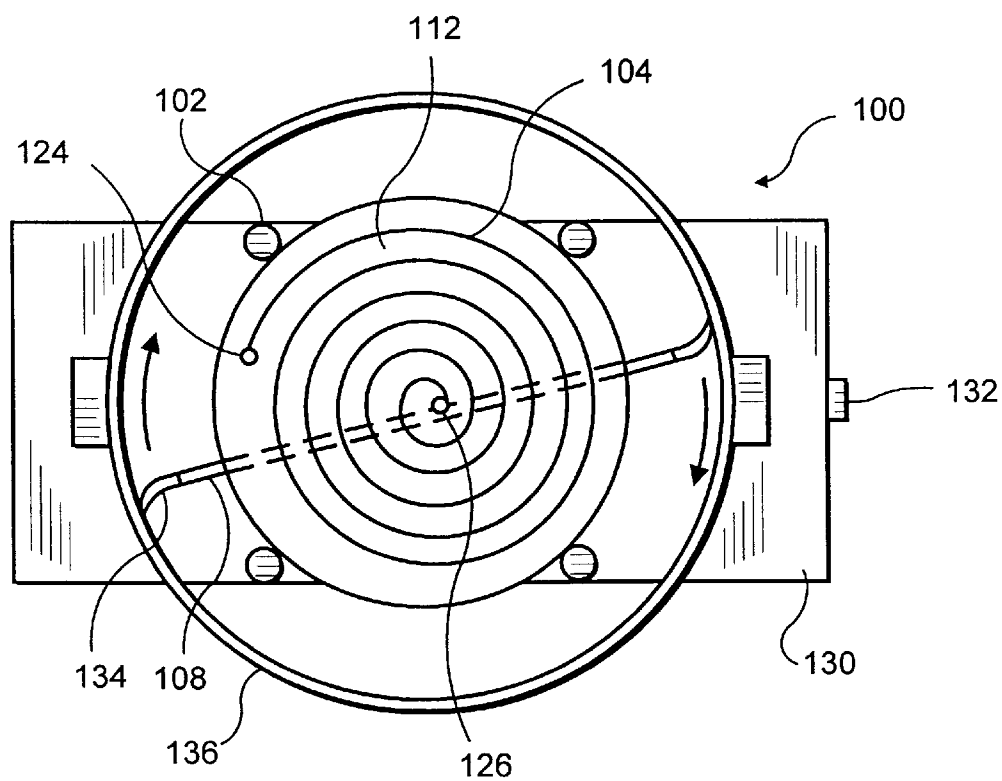
FIG. 8 is a top view of an apparatus for effecting magnetic separation of a magnetic compound.
Figure 9:
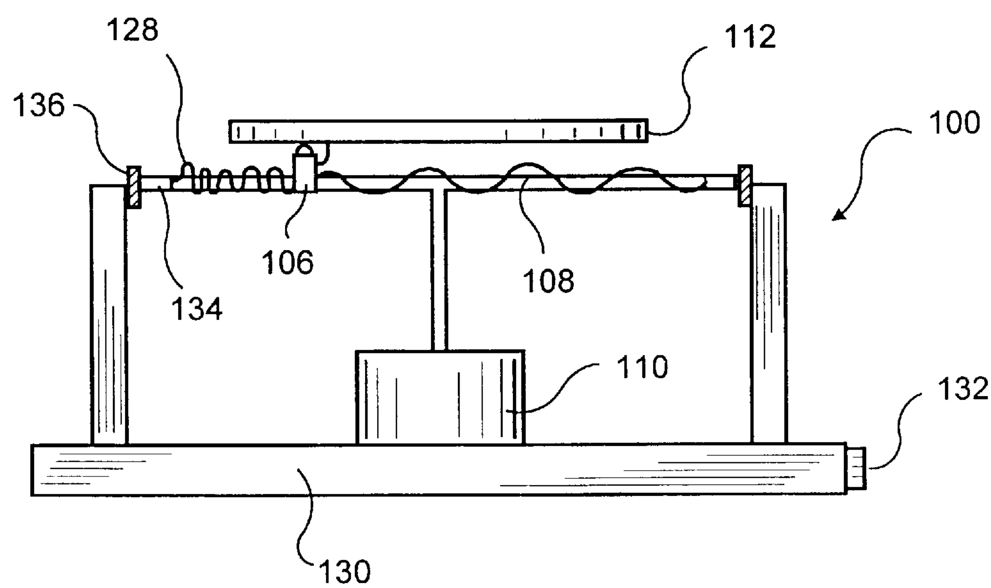
FIG. 9 is a side view of the apparatus of FIG. 8.

One system for performing such a separation is illustrated in FIG. 8 and 9. A substrate 112 is mounted to separation apparatus 100 with mounting pins 102. A separation groove 104 traverses a spiral path across the upper surface of the substrate 112. A magnetic head 106 is mounted below the substrate 112. The magnetic head 106 includes a magnet 122 (FIG. 10), preferably an electromagnet, positioned directly below the separation groove 104. The magnetic head 106 is mounted to a rotator rod 108, which is rotated in the plane of FIG. 8 by a rotator motor 110. The magnetic head 106 is slidable along the rotator rod 108 (i.e., radially with respect to the spiral of the groove 104) to maintain alignment with the separation groove 104.

Figure 11:
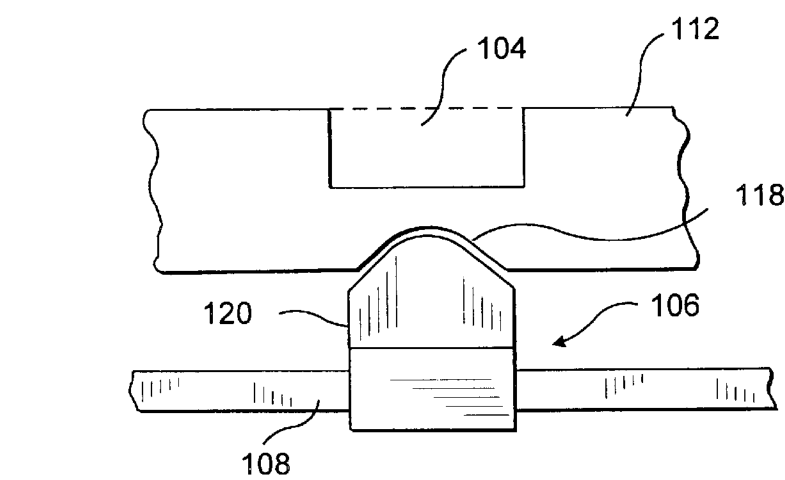
FIG. 11 is a view of an alternative magnet guide arrangement for use with the apparatus of FIGS. 8–9.

The alignment of the magnetic head 106 with the separation groove 104 may be maintained with the use of a guiding groove 114 which accepts a guiding protrusion 116 of the magnetic head 106, as illustrated in FIG. 11. In an alternative arrangement (FIG. 11, the magnetic head 106 includes a shaped magnet 120, while the substrate 112 includes a guiding groove 118 which accepts shaped magnet 120. Numerous alternative arrangements may be provided to keep the magnetic head 106 in alignment with the separation groove 104. For example, the rotator rod 108 may be a threaded rod which can be rotated to adjust the radial position of the magnetic head 106. Also, optical means may be used to guide the magnetic head thus avoiding the need for the guide groove.

The separation groove 104 has a sample entry point 124 at a first end thereof and a sample outlet 126 at an opposite end thereof. In a magnetic sample separation procedure, magnetizable moieties are attached to the components of a sample mixture of compounds of varying molecular weight, such as polynucleotides, proteins, and fragments thereof. The sample is placed at the sample entry point 124. The magnetic head is positioned at the sample entry point 124, and the electromagnet 122 is energized. The rotator motor 110 is activated to rotate the rotator rod 108 to draw the magnetic head along the separation groove 104.

As the electromagnet 122 moves along the separation groove 104, the magnetizable moieties attached to the components of the sample are attracted thereto and are themselves entrained in motion along the separation groove 104. By regulating the size of the magnetizable moieties, it can be assured that each of the sample components within the field of the electromagnet 122 is subject to an approximately equal entraining force. The components of the sample, however, encounter a resistance to their motions through the separation groove 104 which is dependent on the properties of the individual sample components. Where the groove 104 is filled with a separation medium, such as a gel or a liquid suspension medium, the resistance is comparable to the resistance encountered in well-known electrophoresis processes. Where the groove 104 is devoid of a separation medium, the resistance derives from physical surface interactions between the components of the sample and the walls of the groove 104. Centrifugal forces on the sample components in motion around the groove 104 tend to force those components against the outer wall of the groove 104, such that interactions between the outer wall and the components are particularly strong. Variation of the resistance to generate different separation conditions may be effected by changing the separation medium and/or by altering the smoothness and chemical composition of the walls of the groove 104.

Physical processes involving resistance to motion are extremely complex and often difficult to predict. For the purposes of sample separation, it is not necessary to postulate or understand fully the processes underlying the resistance to the motion of sample components; it is only necessary that the overall resistance to motion be a function of a property which differentiates the sample components. It is well understood that the molecular weight of a sample component, for example, has a powerful effect on that component's resistance to motion. Alternatively, a gel may be introduced between the spokes.

As sample components are entrained in motion through the separation groove 104, the sample components with a larger molecular weight, having a greater resistance to motion, travel a shorter distance than the sample components with a smaller molecular weight, thus resulting in separation of the sample components along the separation groove 104.

To effect further separation of the sample components the magnetic head 106 can make repeated passes along the separation groove 104, from the starting point 124 to the ending point 126. To avoid disturbing the positions of the sample components, the electromagnet 122 is preferably shut off while it is being repositioned to the starting point 124. Where the magnet 122 is a permanent magnet, the magnet 122 is preferably disengaged from the substrate 112 and held at a distance therefrom until the magnet 122 is positioned at the starting point 124.

The magnetic sample separator 100 further includes magnetic field reading componentry as illustrated in FIGS. 1–5 and described above. The magnetic field detector 14 is mounted in the magnetic head 106 and is scanned along the separation groove 104 by the rotator motor 110. In a separation procedure including multiple passes of the magnet 122, the magnetic field detector 14 is periodically employed to read the positions of the magnetizable moieties along the separation groove 104. Once the first components of interest are detected by detector 14 to have reached the end 126 of the groove, the separation is stopped. The reading by detector 14 may take place in a reverse direction of motion along the groove 104, thus accomplishing a reading of the sample component distribution as well as repositioning the magnetic head 106 at the start 124 of the separation groove.

The components of magnetic head 106 communicate with a base structure 130 and computer communications port 132 through cables 128 which terminate in electrical contact brushes 134. The electrical contacts 134 form a sliding conductive conduct with a signal contact ring 136, which ultimately communicates with the port 132. Power for the electromagnet 122, is communicated to the magnetic head 106 through this route, and signals from the magnetic field detector 14 travel in the reverse direction through the same route.

Various alternative constructions of the magnetic sample separator 100 are possible. The substrate 112 need not be circular, and the separation groove 104 need not be spiral. Separation can be effected along a linear or arcuate separation groove, and the substrate 112 may be of any shape. The spiral shape of the separation groove 104 is preferred as providing the ability to contain an exceptionally long separation lane on a small substrate area, and the circular shape of the substrate 112 is preferred as providing the most effective use of that area for when a spiral groove is employed. It should also be clear that, while the direction of separation, from start 124 to end 126, is illustrated herein as spiraling inward, the direction may just as well spiral outward.

Various alternatives to mechanical layout of the magnetic separation system 100 are possible and well within the grasp of the ordinary artisan. For example, the separation groove 104 and guide groove 114 may be on the same side of the substrate, or, as mentioned above, the guide groove 114 may be dispensed with. Instead of rotating the magnetic head 106 around the substrate, the substrate may be rotated while the magnetic head 106 merely tracks the radius of the separation groove 104. In one such arrangement, the substrate 112 is rotated like an audio record, and the magnetic head 106 is mounted on a swivel, analogous to the tone arm of a record player, to track the separation groove. In arrangements with a rotating substrate 112, a system of brushes 134 and ring contacts 136 s generally not necessary, allowing for direct wiring from the magnetic head 106 to the communications port 132. Even when the magnetic head 106 is rotated about a stationary substrate, the brushes 134 and ring contacts 136 may be replaced with other signal transmission componentry, such as an optical or otherwise wireless signaling system.

Figure 10:
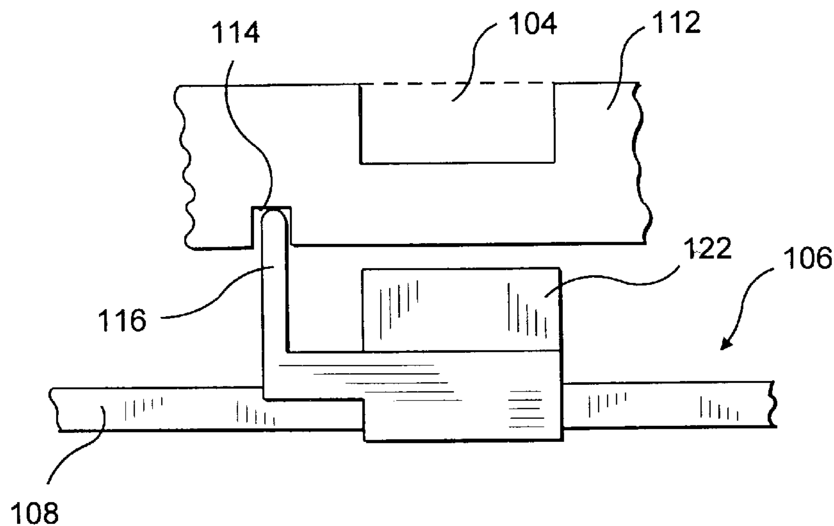
FIG. 10 is a view of a magnet guide arrangement for use with the apparatus of FIGS. 8–9.
Figure 12:
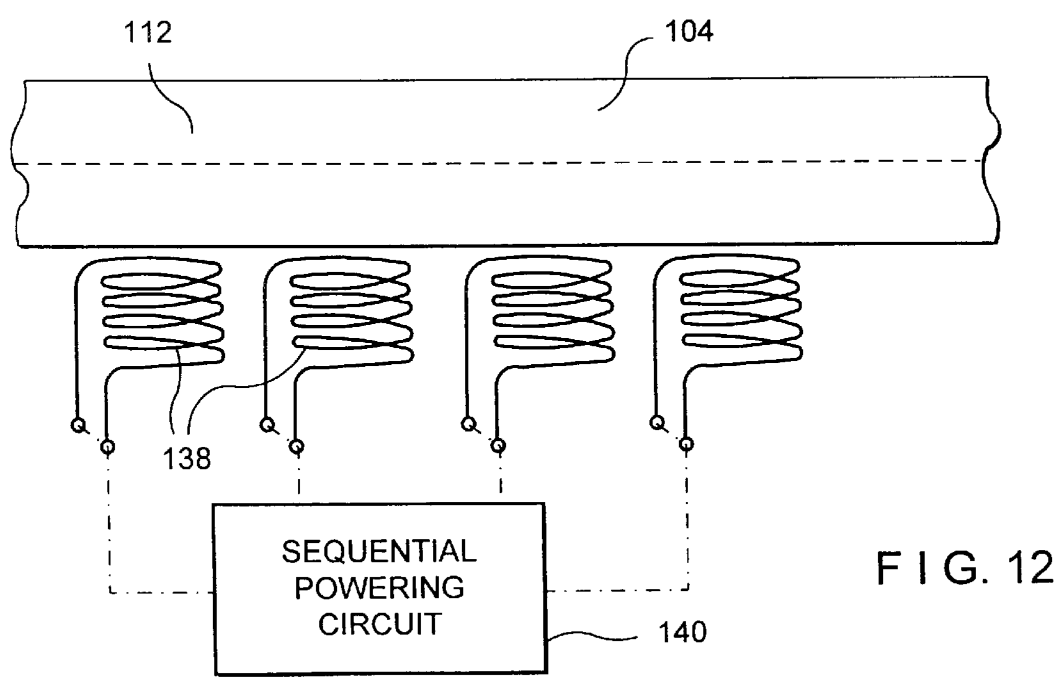
FIG. 12 is a view of a sequential electromagnet arrangement for use with a magnetic separation apparatus.

In FIGS. 8–10, a moving magnet 122 is illustrated as entraining the sample components. As illustrated in FIG. 12, however, the moving magnet may be replaced by a series of electromagnets 138 powered by a sequential powering circuit 140. Sequential powering circuit 140 sequentially energizes the electromagnets 138 to emulate the effects of a single moving electromagnet. Electromagnets 138 may overlap to provide a smooth transfer of the magnetic field along the separation groove 104.

Centrifugal Separation

Figure 13:
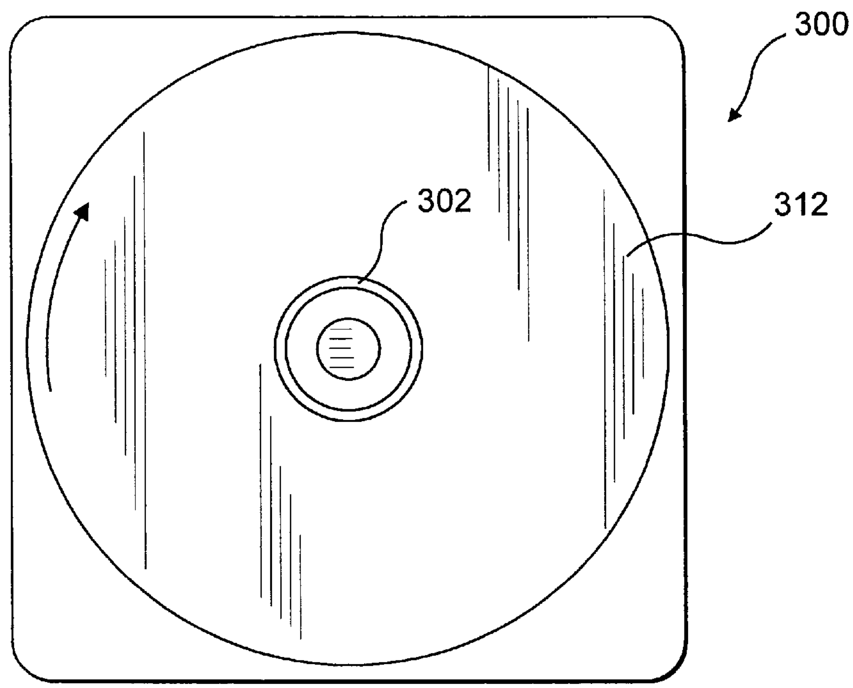
FIG. 13 is a top view of an apparatus for centrifugal separation of a sample mixture using a porous separation medium.

An alternative separation apparatus 300 is illustrated in FIG. 13. Separation apparatus 300 includes a disk-shaped porous separation substrate 312, such as an acrylamide or agarose gel, with a concentric sample groove 302. A sample mixture is placed in the groove 302, and the separation substrate 312 is rotated to generate a centrifugal force on the sample components. The centrifugal forces on the sample components force the sample components outward through the separation substrate 312 toward the circumference thereof. Sample components of greater molecular size will travel more slowly through the porous substrate 312 than sample components of smaller molecular size, resulting separation of the sample components and leading to “rings” of separated material.

Magnetizable moieties may be attached to the components of the sample either before or after sample separation for magnetic detection of the bands, or the bands may be detected using conventional staining or marker techniques.

Figure 14:
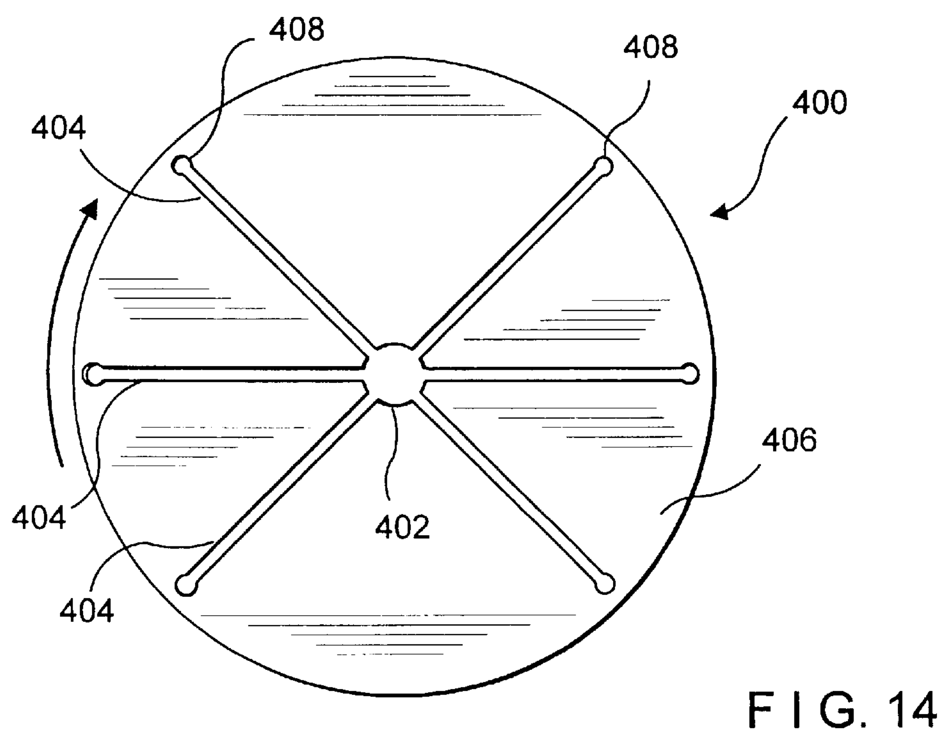
FIG. 14 is a top view of an apparatus for centrifugal separation of a sample mixture using radial separation lanes.

In another separation system 400, illustrated in FIG. 14, a central sample well 402 is provided in a disk 406, with several radial separation spokes 404 extending therefrom. The separation spokes 404 may be grooves on a surface of the disk 406. Alternatively, the separation spokes 404 may be enclosed tubules passing through the disk 406. The disk 406 is rotated, providing a centrifugal force on a sample in the sample well 402. As discussed above with respect to the magnetic separator of FIGS. 8–12, the movement of sample components through a substrate is dependent on a number of factors, including interactions between the sample components and a substrate wall. The separation spokes 404 have a variety of diameters to introduce a further controlled variable to the separation process.

First, the statistical likelihood of a sample component entering one of the spokes 404 is dependent on the size of the sample component and the diameter of the spoke. Thus, larger sample components are relatively more likely to enter the larger-diameter spokes, while smaller sample components are more likely to enter the smaller-diameter spokes. Second, the separation spokes with smaller diameters result in a higher level of interaction between the sample components and the spoke surfaces and thus a higher level of resistance to movement, whereas those with larger diameters have less sample-surface interaction and a lower level of resistance to movement.

Magnetizable moieties may be attached to the components of the sample either before or after sample separation, or the separated sample may be detected using conventional dyeing techniques. The variety of separation spoke diameters can be taken advantage of in a number of ways. If the rotation of the disk 406 is stopped while sample components remain inside the spokes 404, the separations in different spokes can be compared and cross-checked. Light components which may have passed through to the end of one of the larger spokes may still be present in one of the narrower spokes. A collection well 408 may be positioned at the circumferential end of each spoke 404. The separation can be carried out until sample portions collect in the collection wells 408. The sample portions in collection wells 408 at the ends of narrower spokes 404 will be richer in smaller sample components, while the sample portions collected in collection wells 408 at the ends of wider spokes 404 will be richer in heavier sample components. Of course, the separation can be carried out repeatedly to effect a further refined separation.

What is claimed is:

1. An apparatus for separating a mixture of compounds having different molecular sizes selected from the group consisting of polynucleotides, proteins and fragments thereof, the compounds having magnetized moieties attached thereto comprising:

a) a support having a separation lane therein, the separation lane providing resistance to movement of the compounds therealong, the resistance being proportional to the molecular size of the compounds, the separation lane having a starting end and a terminal end;

b) a magnet positioned to provide an attractive force on the magnetized moieties contained in the separation lane;

c) a guide for maintaining the magnet in proximity to the separation lane; and d) a drive for moving the magnet along the length of the separation lane to entrain at least some of the compounds attached to the magnetized moieties during their movement along the separation lane.

2. An apparatus for separating a mixture of compounds having different molecular sizes selected from the group consisting of polynucleotides, proteins and fragments thereof, the compounds having magnetized moieties attached thereto comprising:

a) a separator wheel, the separator wheel including a sample reservoir at a central portion thereof for receiving a liquid sample containing said compounds, the separator wheel further having a plurality of radial channels in communication with the sample reservoir and extending outwardly from the sample reservoir, each channel having a cross-sectional size different from the cross-sectional size of at least one other channel; and b) a drive for rotating the separator wheel around the reservoir.

* * * * *